(12) United States Patent
DiCesaro

(10) Patent No.: US 10,342,991 B2
(45) Date of Patent: Jul. 9, 2019

(54) PHOTONIC TREATMENT APPARATUS

(71) Applicant: Anthony J. DiCesaro, Pittsburgh, PA (US)

(72) Inventor: Anthony J. DiCesaro, Pittsburgh, PA (US)

( * ) Notice: Subject to any disclaimer, the term of this patent is extended or adjusted under 35 U.S.C. 154(b) by 0 days.

(21) Appl. No.: 14/882,001

(22) Filed: Oct. 13, 2015

(65) Prior Publication Data

US 2016/0101295 A1 Apr. 14, 2016

Related U.S. Application Data

(60) Provisional application No. 62/062,522, filed on Oct. 10, 2014.

(51) Int. Cl.
 *A61N 5/06* (2006.01)

(52) U.S. Cl.
 CPC .... *A61N 5/0616* (2013.01); *A61N 2005/0643* (2013.01); *A61N 2005/0652* (2013.01); *A61N 2005/0663* (2013.01)

(58) Field of Classification Search
 USPC .................................. 607/77–95; 606/2–19
 See application file for complete search history.

(56) References Cited

U.S. PATENT DOCUMENTS

| | | | | |
|---|---|---|---|---|
| 5,944,748 A | * | 8/1999 | Mager | A61N 5/0601 606/11 |
| 6,447,537 B1 | * | 9/2002 | Hartman | A61N 5/0616 607/90 |
| 9,498,641 B2 | | 11/2016 | Ward | |
| 9,808,314 B2 | | 11/2017 | Ward | |
| 2004/0166146 A1 | * | 8/2004 | Holloway | A61F 15/00 424/449 |
| 2007/0135872 A1 | * | 6/2007 | Sumitomo | A61N 5/0616 607/90 |
| 2014/0257439 A1 | * | 9/2014 | Douglas | A61N 5/0618 607/90 |
| 2014/0277294 A1 | * | 9/2014 | Jones | A61N 5/062 607/88 |
| 2014/0288351 A1 | * | 9/2014 | Jones | A61N 5/06 600/9 |
| 2014/0338819 A1 | * | 11/2014 | Hong | B65H 23/26 156/160 |
| 2015/0025602 A1 | * | 1/2015 | Wagenaar Cacciola | A61N 5/0616 607/94 |

* cited by examiner

*Primary Examiner* — Niketa I Patel
*Assistant Examiner* — Vynn V Huh
(74) *Attorney, Agent, or Firm* — The Webb Law Firm

(57) ABSTRACT

A photonic treatment apparatus and apparatus for patient care, using a film, such as a phosphorous plate and a casing comprising an aperture provided for films that may be positioned therein to allow for desired treatments of a user, a photonic engine, positioned behind the film, to create photonic pressure. The photonic engine directed toward the film energizes the film achieving a desired wavelength emanation, a first zone of wavelengths that originate from the photonic engine, and a second zone of wavelengths emanating from the film that can be directed toward a target area and used in a method for treating patient conditions. A specific phosphor plate can be used for a desired treatment to customize the output to a specific wavelength necessary for treatment of specific conditions or other possible uses.

13 Claims, 15 Drawing Sheets

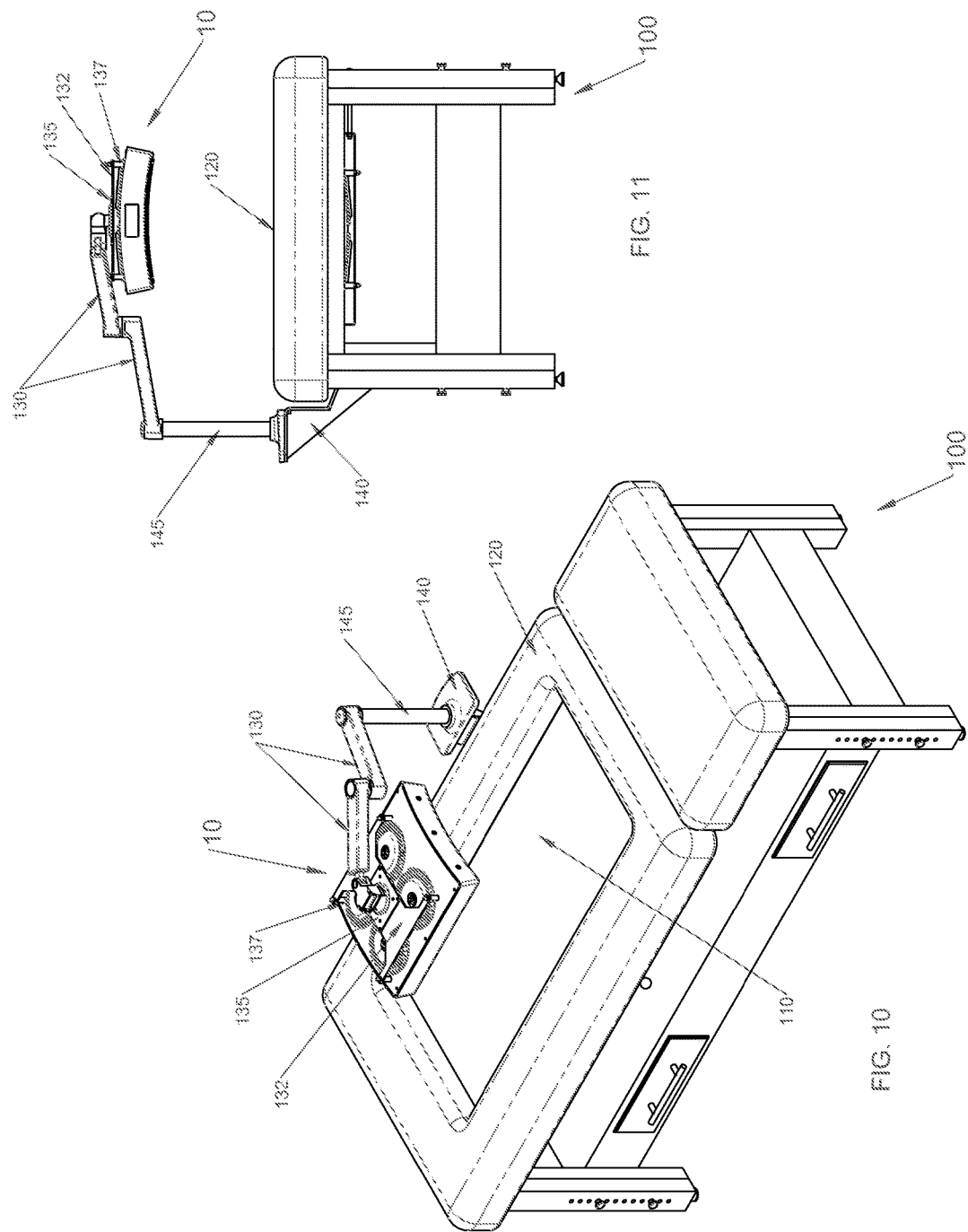

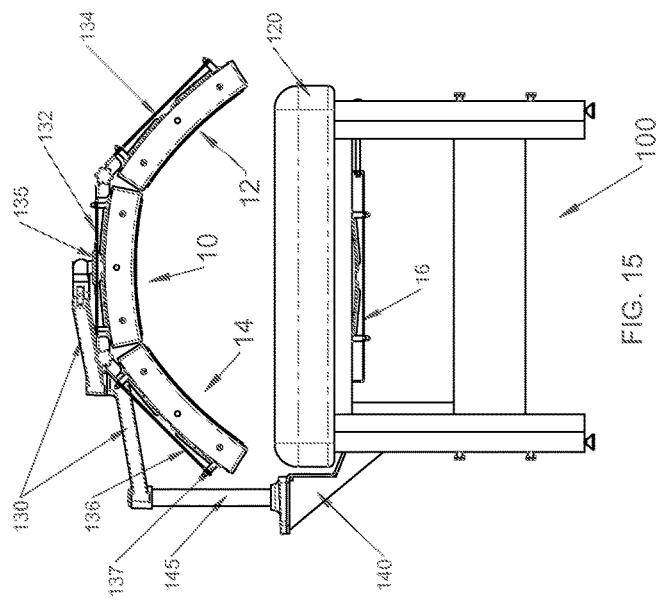
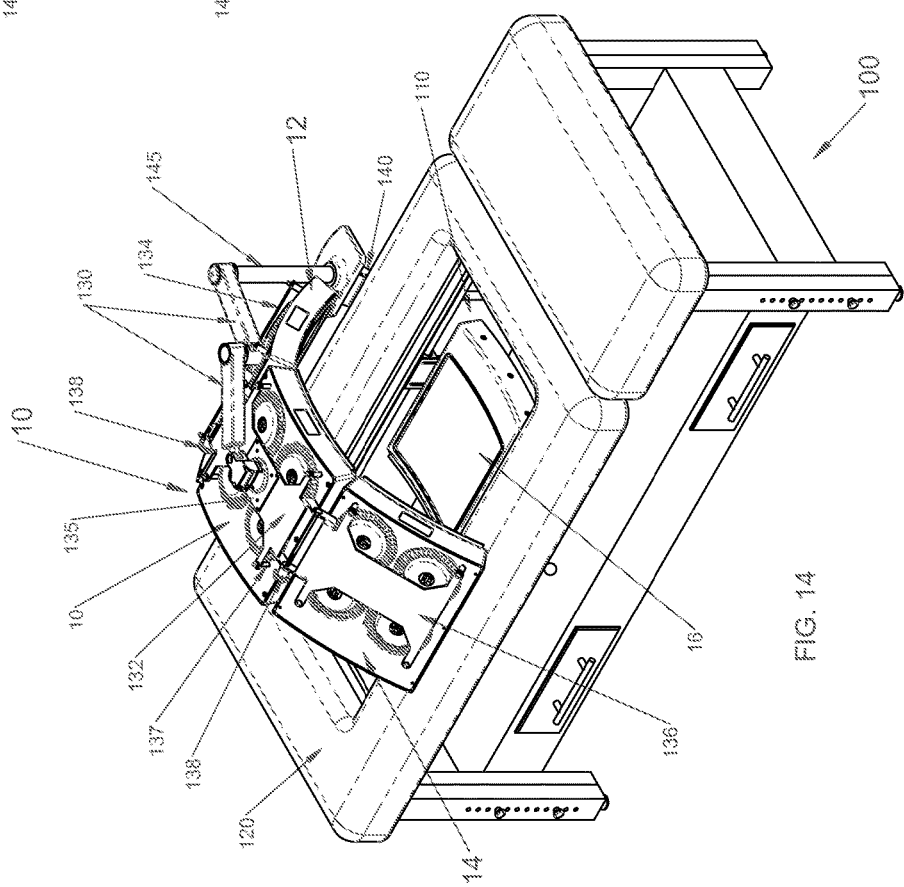

PHOTONIC TREATMENT APPARATUS

CROSS REFERENCE TO RELATED APPLICATION

This application claims the benefit of U.S. Provisional Application No. 61/062,522, filed Oct. 10, 2014, the disclosure of which is herein incorporated by reference in its entirety.

BACKGROUND OF THE INVENTION

Field of the Invention

The present invention, in one embodiment, relates generally to a photonic treatment apparatus and related methods, and, more particularly, to a treatment apparatus having photonic emitters and films for custom low-temperature treatments of a user in one or more sizable areas of interest. In another embodiment, the present invention relates generally to a lighting source used to grow plants.

Description of Related Art

Various procedures in the healthcare field and otherwise, use various emitters to treat patients for various ailments or elective treatments. These emitters vary based upon the needed treatment and may include electromagnetic radiation, lower power laser, LED, etc.

It is well known that there are limitations with current photonic treatment systems. One limitation is the inability of systems to provide deep penetration on the photonic treatment area if the source light is not strong enough. However, lasers also can have damaging effects to the user if the performance of the laser is increased beyond the ability of the target area to receive such intensities.

Further, state of the art photonic treatment systems often rely upon low-level lasers having higher cost with a low output pattern. These more focused light patterns make it difficult to treat larger areas effectively without adding further costs and complications, not to mention generate noticeable amounts of heat. However, because of the ability to have focused light pattern distributions, such technologies are common in treatment systems on specific regions of a treatment area.

Another limitation is the limited use of varying treatments once the photonic laser light sources are installed and used in a device. Thus, multiple pieces of equipment may be needed, or cumbersome light source changes may be required to vary treatments.

In reference to lighting sources used to grow plants, whatever the medium is that plants are grown in, from soil to hydroponics, sufficient lighting with reduction of electrical energy usage is the optimal goal of any gardener. Using lamps that generate less heat reduces fire risks from overtaxed wiring systems and plant damage or even combustion if they grow close to the lamp, along with reduced need for fans and cooling systems.

Full spectrum LED lamps use much less electricity and aim to provide a more precise delivery of the desired frequencies of light ranging from 420 nanometers (nm) to 750 nm that will grow your plants from seed to harvest. Getting the necessary intensity of light can prove to be a costly investment because of the need for many different types of light. Many growers are satisfied with the results obtained by using 1000 watt full spectrum LED lights.

SUMMARY OF THE INVENTION

Accordingly, it is one object of the present invention to provide a photonic treatment apparatus, using a photonic engine and one or more films, which is able to treat large target areas of a user with uniform and versatile solutions that overcome the drawbacks of the prior art.

A photonic treatment apparatus for patient care, comprising: a film and a casing comprising: an aperture provided for one or more films that may be positioned therein to allow for desired treatments of a user, a photonic engine positioned behind the film to create photonic pressure, the photonic engine directed toward the film energizes the film achieving a desired wavelength emanation, a first zone of wavelengths that originate from the photonic engine, and a second zone of wavelengths emanating from the film directed toward a target area, wherein the second zone of wavelengths is different from and energized by the first zone of wavelengths, such that the photonic treatment device provides treatment of the target area.

The film may be comprised of a phosphorous plate or other desirable wavelength-modifying substrate. A specific phosphor plate can be used for a desired treatment to customize the output to a specific wavelength necessary for treatment of specific conditions. The modality of wavelength can be configured as needed by the user for any variety of desired treatments for common conditions. The film can be selectively inserted or removed from the aperture for adjusting the intensity for a desired treatment.

At least one of the target areas of treatment is skin on the patent. The target area of the skin can include skin cells affected by common conditions, for example, psoriasis, eczema, shingles, or acne.

The film may further provide multiple mode wavelengths to disassociate molecules for deeper penetration of light energy into the target area. The photonic engine can include a plurality of LEDs. Varying LEDs can be used to generate higher or lower wavelengths of light to drive a conversion through the film. The second zone of wavelengths emits radiation with a wavelength in the 600-700 nanometer range. The second zone of wavelengths can be adjusted by a processor embedded in the casing or onboard the casing. The processor can automatically adjust the film to the proper color or other property. The skin is irradiated during a first period of time, at predetermined intervals.

The invention further includes a method of treatment using a photonic treatment apparatus, that can include positioning a patient on a photonic treatment apparatus, where said apparatus having a film and a casing comprising an aperture provided for one or more films that may be positioned therein to allow for desired treatments of the user, selecting a specific film for a desired treatment to customize the output to a specific wavelength necessary for treatment of specific conditions; and positioning a photonic engine behind the film to create photonic pressure, the photonic engine directed toward the film energizes the film achieving a desired wavelength emanation directing a second zone of wavelengths emanating from the film toward a target area of the patient, wherein the second zone of wavelengths is different from and energized by a first zone of wavelengths, such that the photonic treatment device provides treatment of the target area. The desired wavelength is a result of energizing the first wavelength. The desired wavelength can be increased during said energization. The desired wavelength can be changed by replacing a film in an aperture of the photonic treatment apparatus. The film can be a phosphor plate. The desired wavelength can be focused and directed toward a target area.

The invention further includes a photonic apparatus, that can include a film and a casing comprising an aperture provided for one or more film that may be positioned therein to allow for desired treatments of the user, a photonic engine, positioned behind the film, to create photonic pressure, the photonic engine directed toward the film energizes the film achieving a desired wavelength emanation, a zone of wavelengths emanating from the film directed toward a target area, wherein the zone is energized by a first source, such that the device provides energized wavelengths customized for a specific purpose.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended to unduly limit the present invention. As used in the specification and the claims, the singular form of "a", "an", and "the" include plural referents unless the context clearly dictates otherwise.

BRIEF DESCRIPTION OF THE DRAWINGS

FIG. 10 is a perspective view of an embodiment of a photonic treatment apparatus as it may be employed with a photonic treatment table in accordance with the present invention;

FIG. 11 illustrates the photonic treatment table shown in FIG. 10;

FIG. 14 is a perspective view of an embodiment of a series of three photonic treatment apparatuses as they may be employed with the photonic treatment table in accordance with the present invention;

FIG. 15 is a front view of the three photonic treatment apparatuses as they may be employed with the photonic treatment table shown in FIG. 14;

DESCRIPTION OF THE PREFERRED EMBODIMENTS

Figure 1:
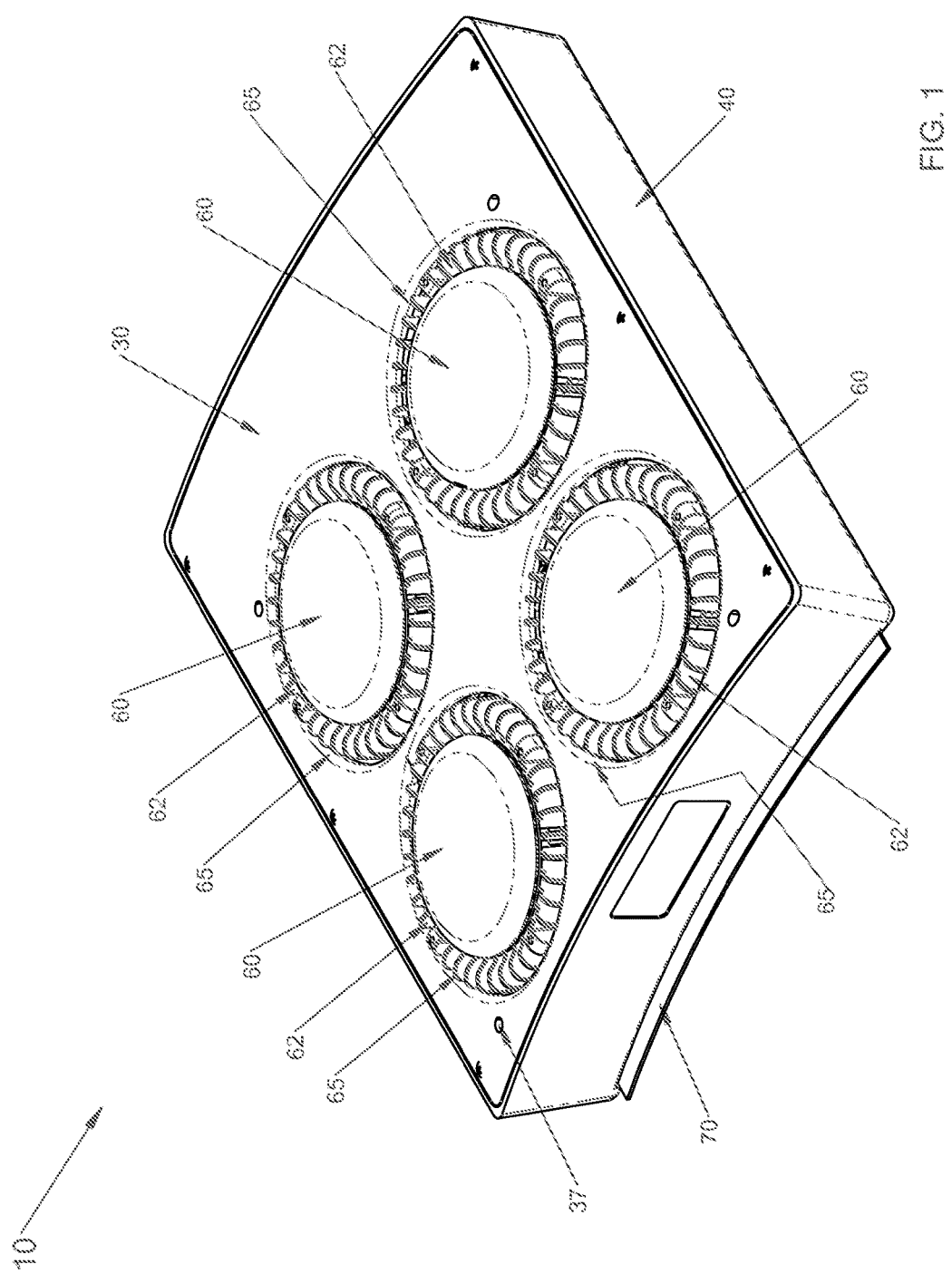
FIG. 1 is a perspective view of an embodiment of a photonic treatment apparatus in accordance with the present invention.

For purposes of the description hereinafter, the terms "upper", "lower", "right", "left", "vertical", "top", "bottom", "lateral", "horizontal", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as unduly limiting.

One embodiment of the present invention is directed to a photonic treatment apparatus 10 that can be powered by medical grade power supplies, that is illustrated in various preferred and non-limiting embodiments in FIGS. 1-17 of the present invention. The photonic treatment apparatus 10 may be provided with an upper casing 30, a lower casing 50, and an outer casing 40. These casings 30, 40, 50 may generally be placed in connection forming a cover and provided to protect the inner workings and componentry of the photonic treatment apparatus 10. The upper casing 30 may also be provided with one or more apertures 37 for enabling attachment of various supports for the photonic treatment apparatus 10. In addition, the casings 30, 40, 50 may provide for an enclosed non-contact photonic treatment apparatus 10 that reduces sanitary issues when employed with a user.

The upper and lower casings 30, 50 may have a cambered configuration to assist in the directional photonic treatment of a user (not shown), wherein lower casing 50 may have a smaller surface area than the upper casing 30 to provide an increased flux or photonic pressure/density on the target area. In addition, the casings 30, 40, 50 may be comprised of a light-weight material for assisting with ease of positioning as well as Acrylonitrile Butadiene Styrene reflector material to increase light emissions.

The photonic treatment apparatus 10 may further include one or more fans 60. The fans 60 can be positioned within one or more heat sinks 62, which may be positioned inside an aperture 65 of the upper casing 30. Fans 60 may be comprised of a diaphragm fan, for example, or other means for cooling and/or in combination with heat sinks 62 shown in at least FIGS. 1-6. Heat sinks 62 may be comprised of aluminum or other material having favorable heat transfer properties.

As can be seen in FIG. 1, for example, the fans 60 and heat sinks 62 may be positioned through the upper casing 30 such that they are each angled to dissipate heat in divergent directions. Further, the fans 60 and heat sinks 62 may be configured in a puck-shaped design to facilitate ease of repair and replacement if necessary.

Figure 2:
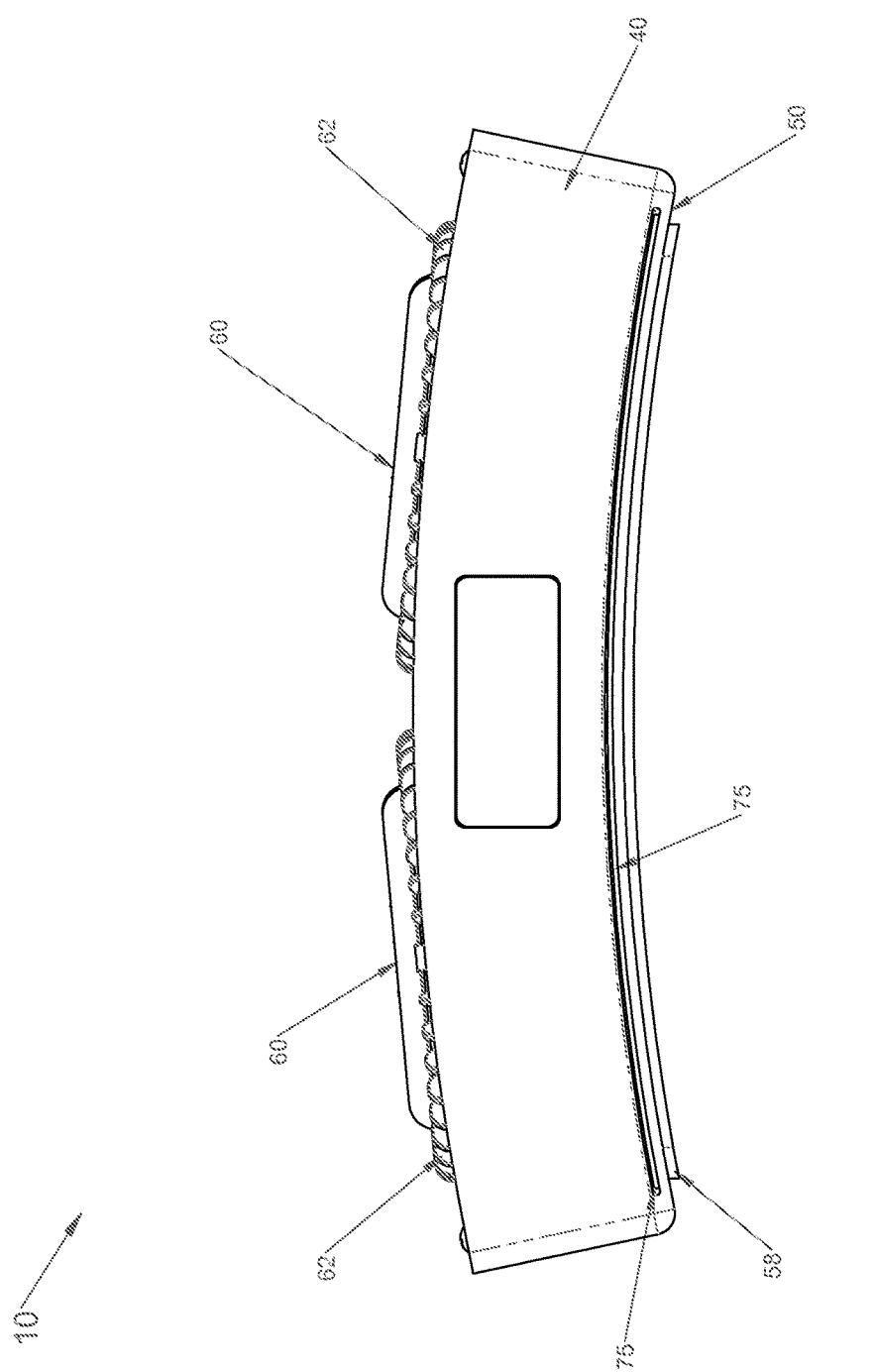
FIG. 2 is a front view of the photonic treatment apparatus shown in FIG. 1.
Figure 3:
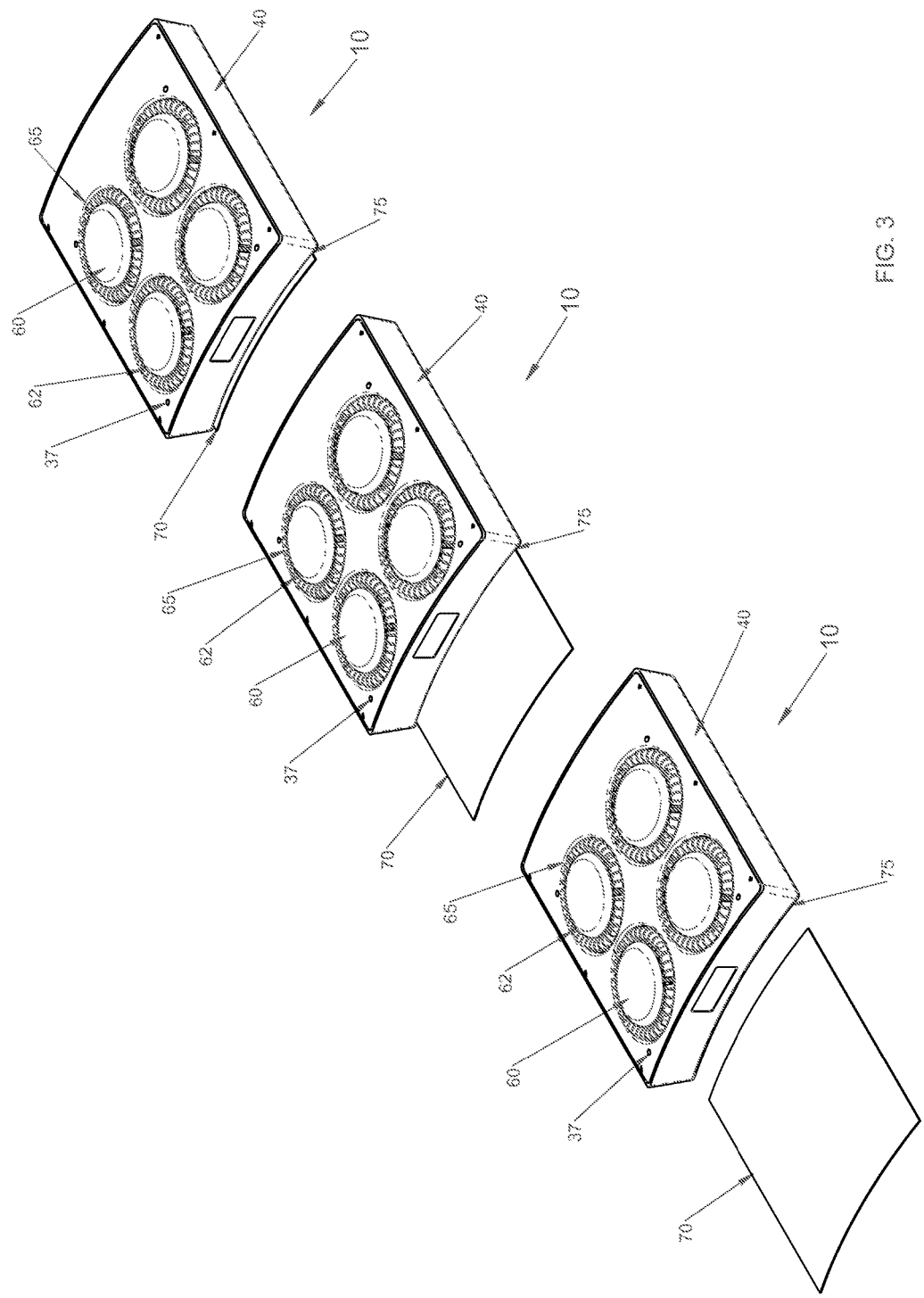
FIG. 3 illustrates how film can be inserted within the photonic treatment apparatus shown in FIG. 1.
Figure 4:
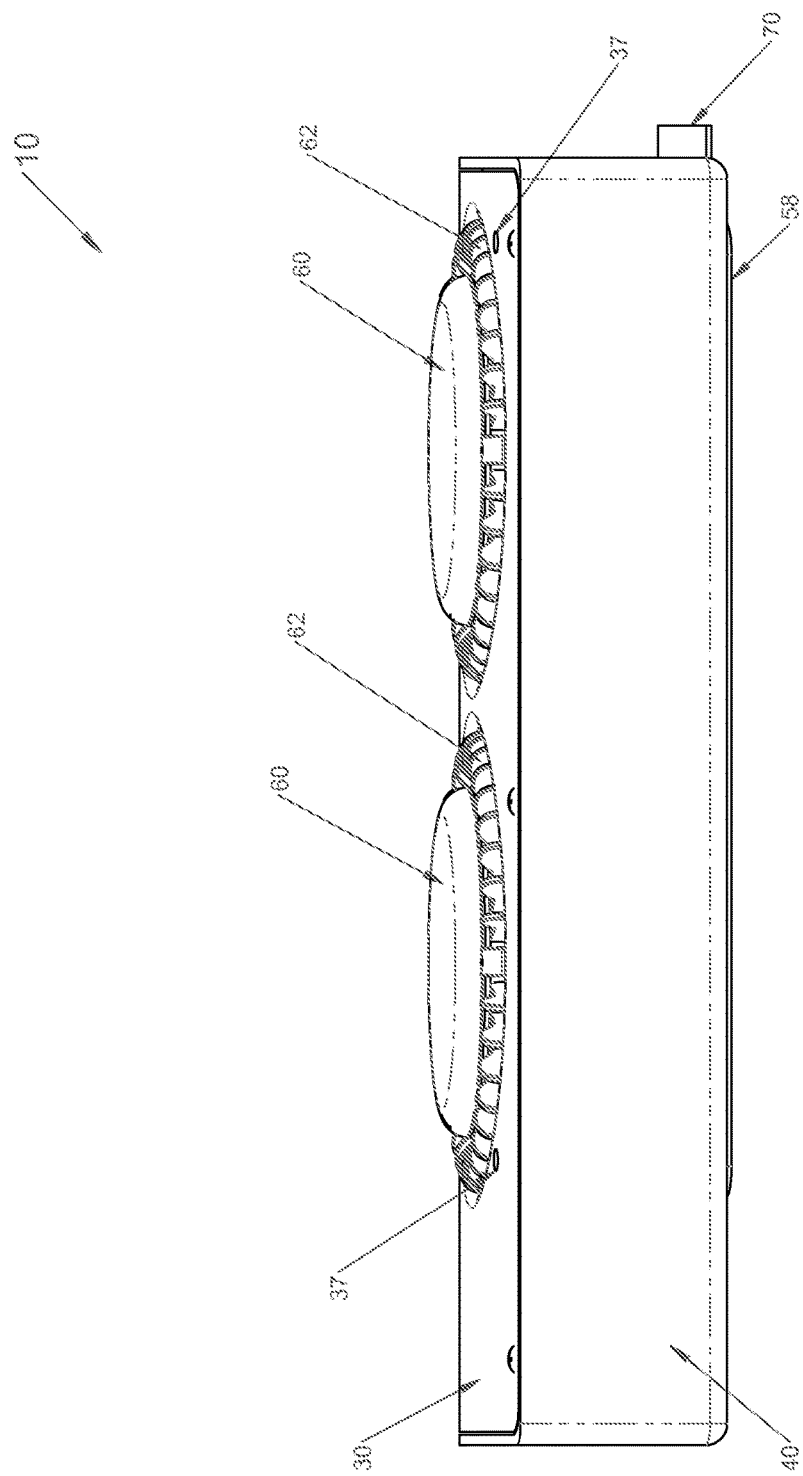
FIG. 4 is a side view of the photonic treatment apparatus shown in FIG. 1.
Figure 5:
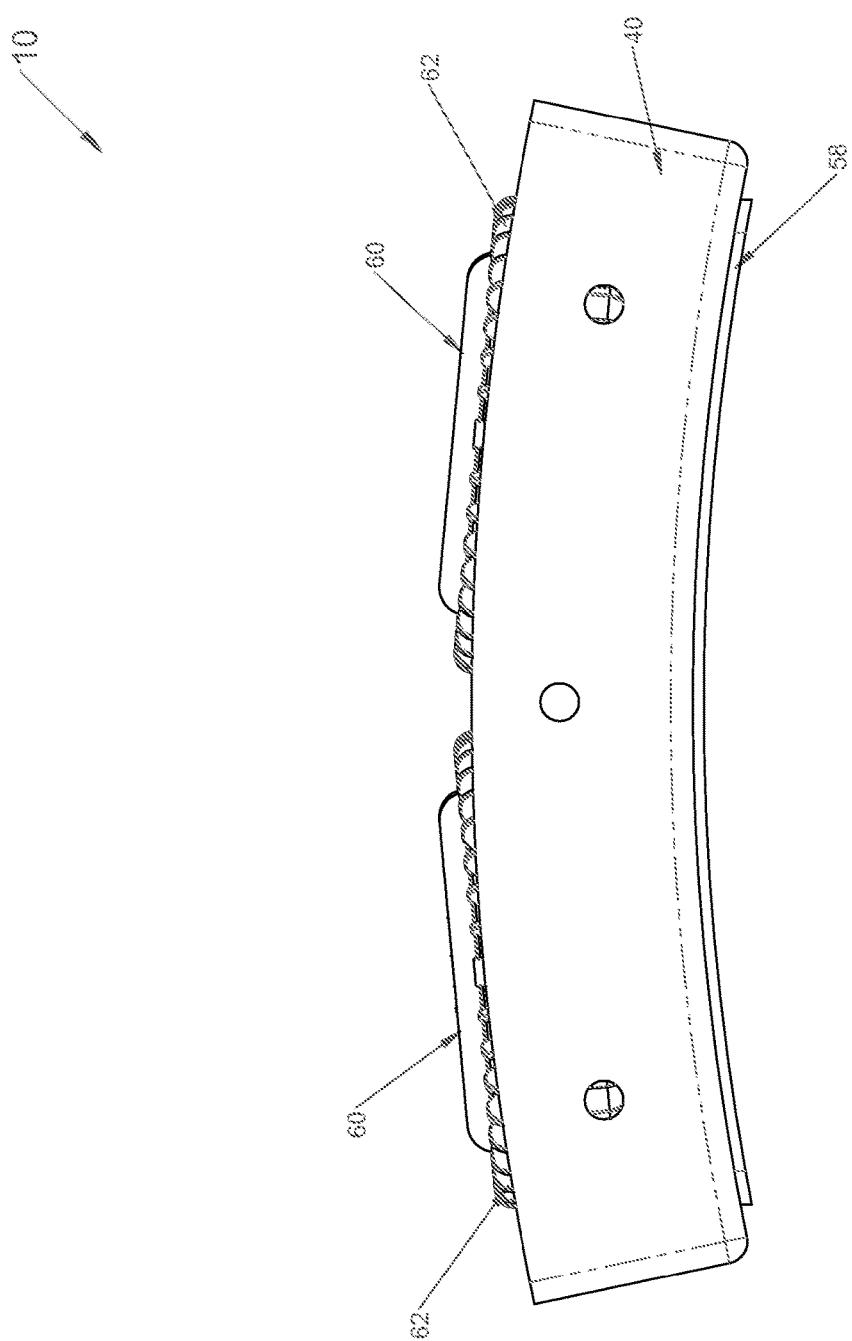
FIG. 5 is a rear view of the photonic treatment apparatus shown in FIG. 1.
Figure 6:
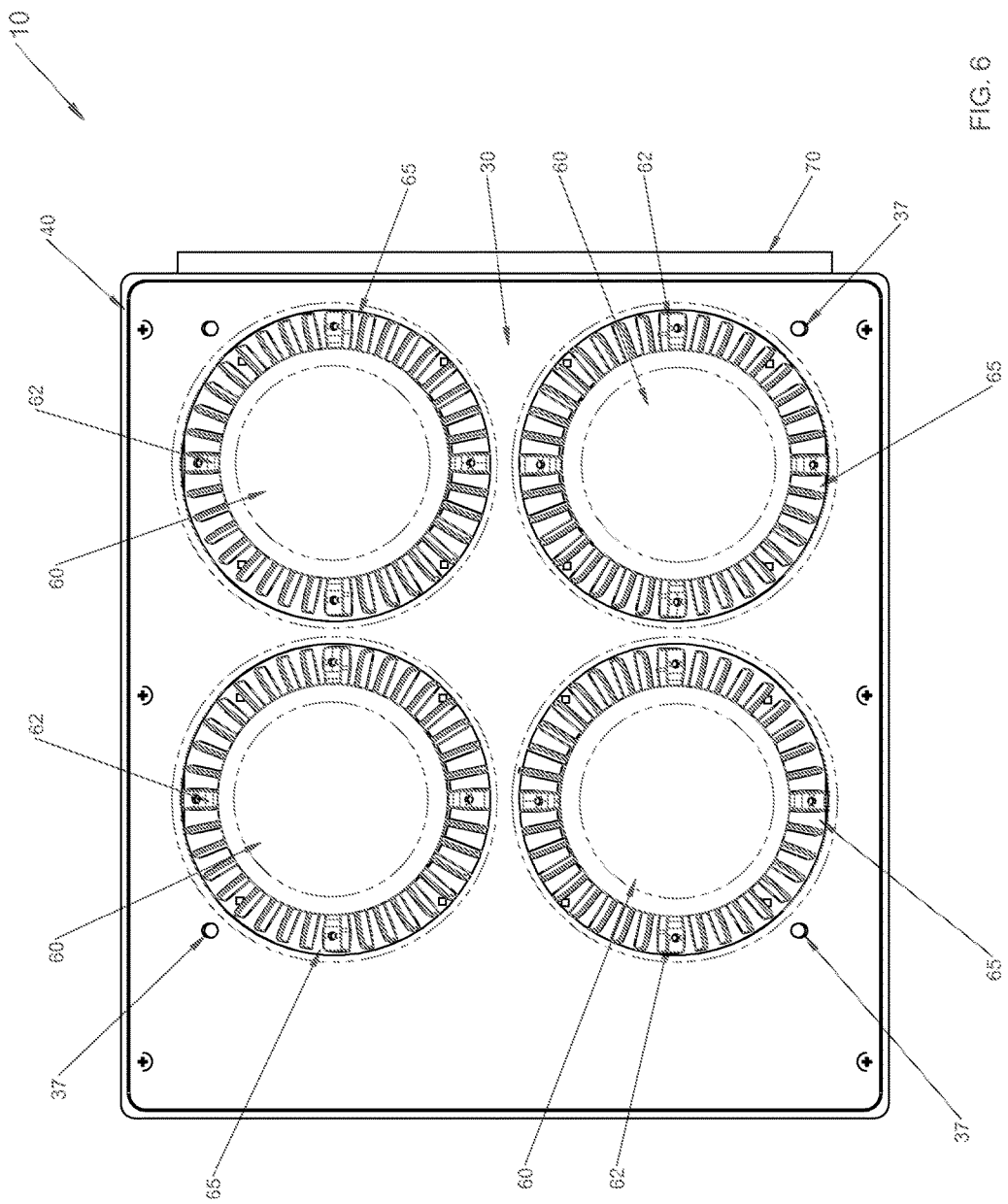
FIG. 6 is a top view of the photonic treatment apparatus shown in FIG. 1.

As can be seen in FIGS. 2-3, the outer casing 40 may have an aperture 75 provided for one or more films 70 that may be positioned therein. Such film 70 may be comprised of a phosphorous plate, or other desirable wavelength-modifying substrate, to allow for desired treatments of the user. The film 70 may further provide multiple mode wavelengths to disassociate molecules for deeper penetration of the light energy into the target area of treatment on the user. Thus, the film 70 may be selectively inserted or removed from the aperture 75, as shown in FIG. 3, depending upon the desired treatment and/or intensity of the wavelengths. Accordingly, the modality of wavelengths may be configured as needed by the user for any variety of desired treatments for common conditions such as, for example, psoriasis, eczema, shingles, acne, etc.

Figure 7:
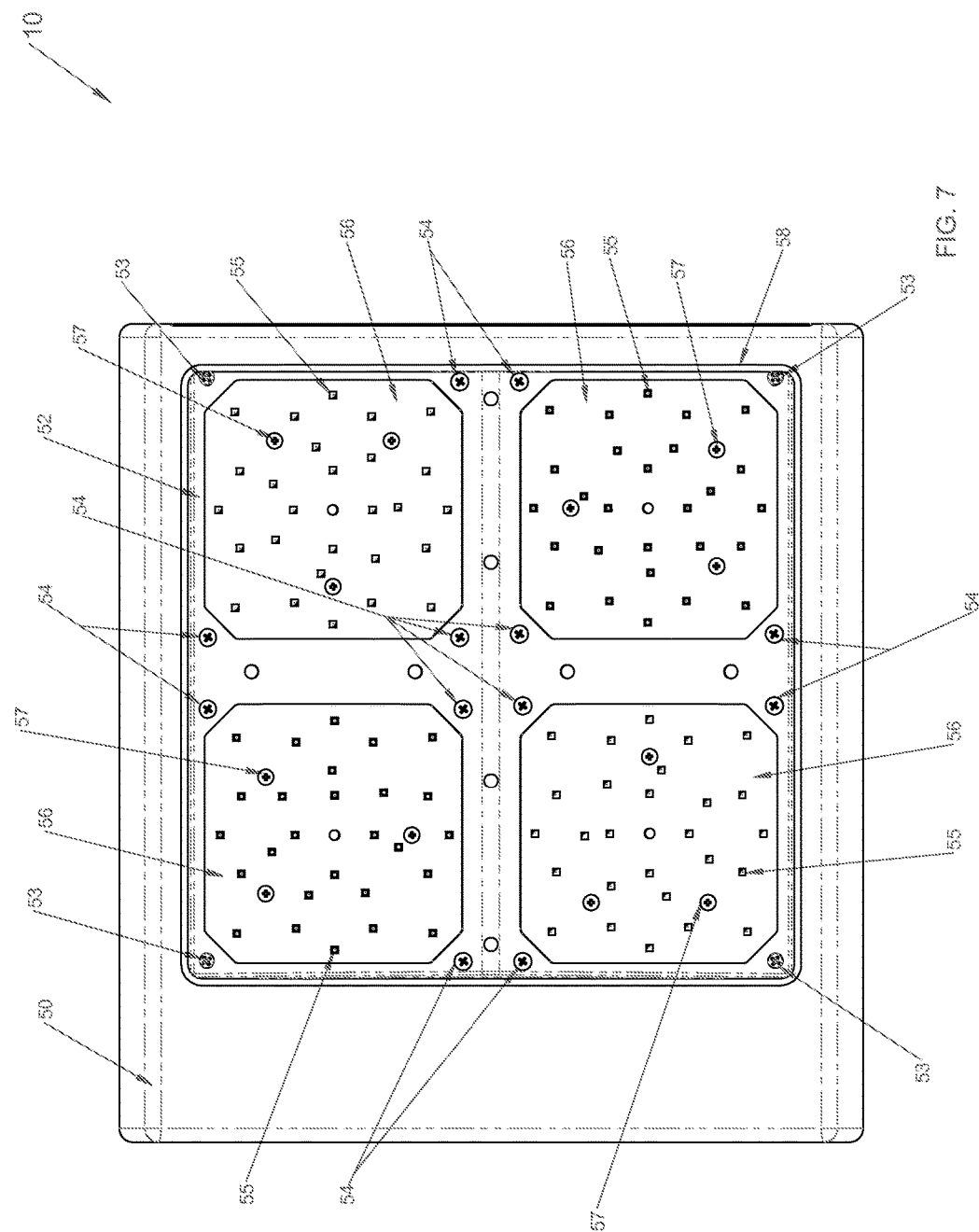
FIG. 7 is a bottom view of the photonic treatment apparatus shown in FIG. 1.
Figure 8:
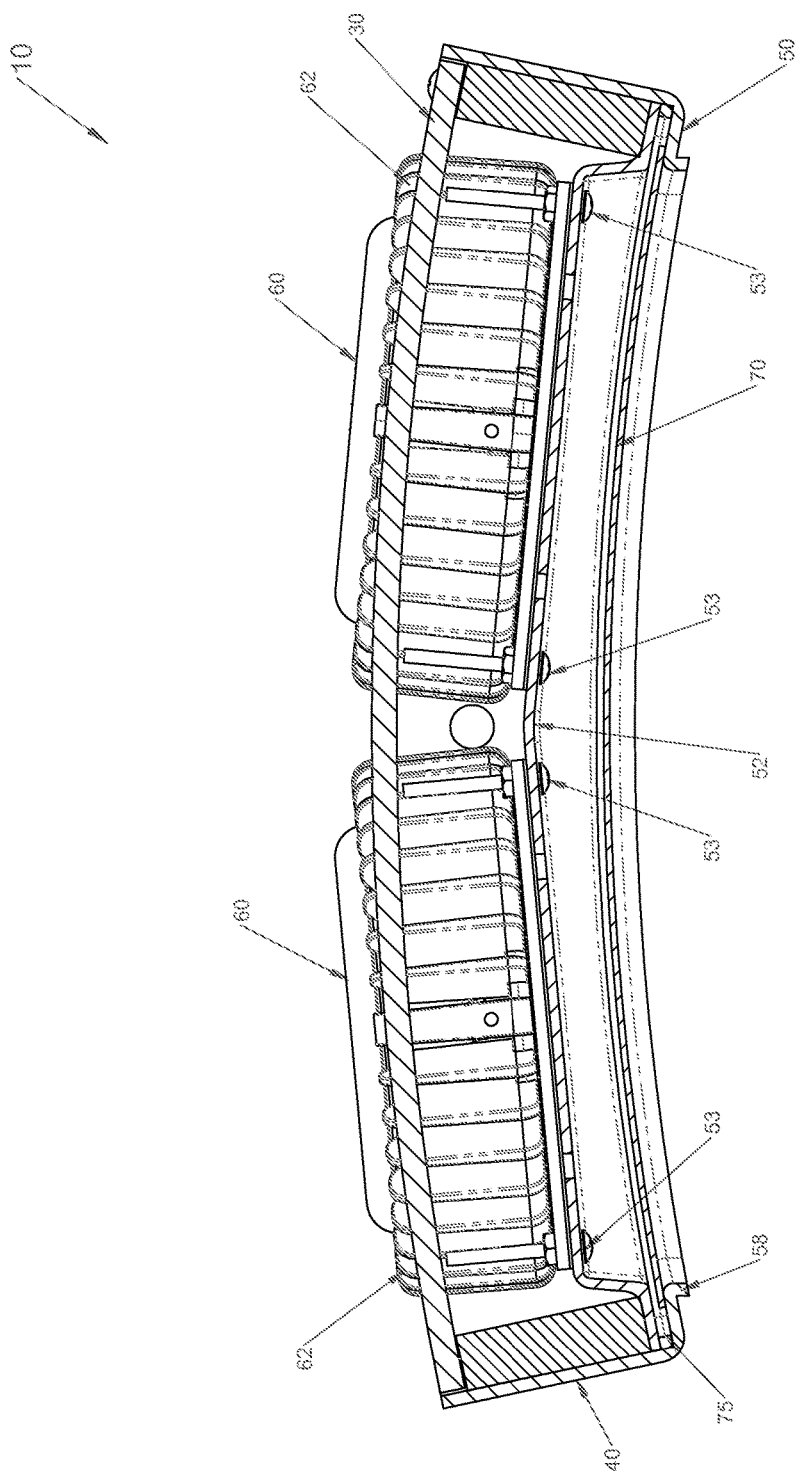
FIG. 8 is a rear sectional view, taken along the lines A-A, of the photonic treatment apparatus shown in FIG. 1.
Figure 9:
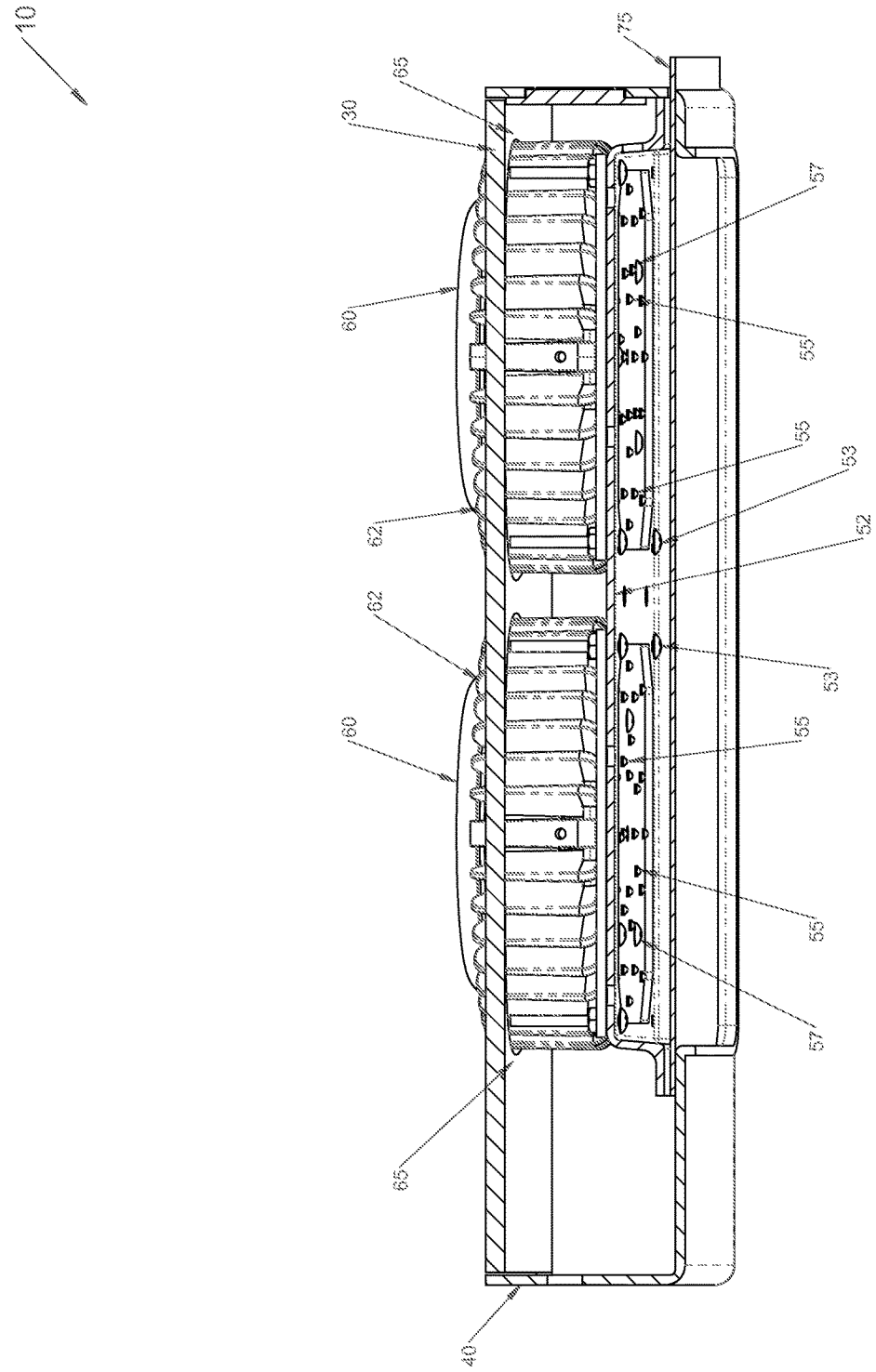
FIG. 9 is a side sectional perspective view, taken along the lines 8-8, of the photonic treatment apparatus shown in FIG. 1.
Figure 13:
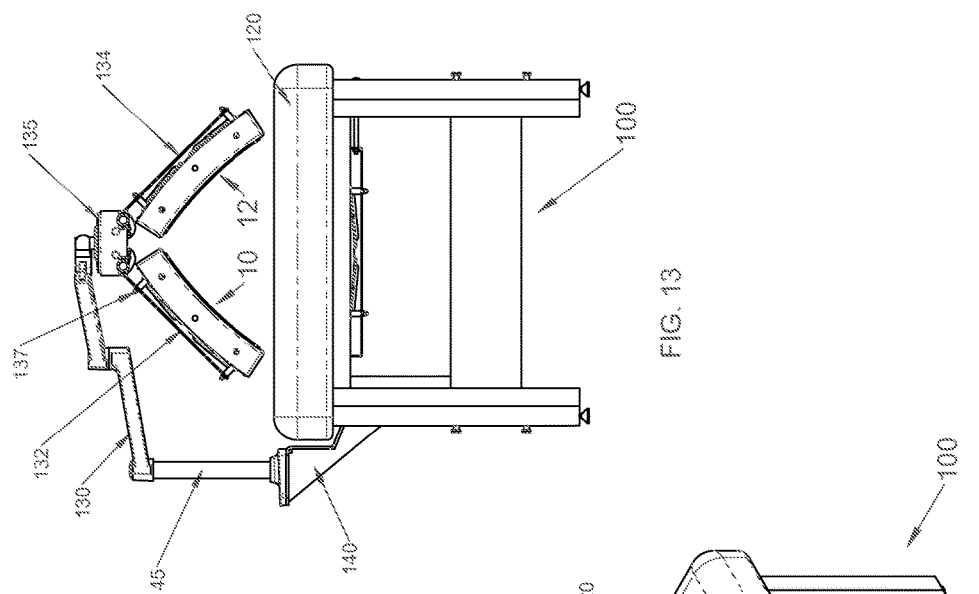
FIG. 13 is a front view of the two photonic treatment apparatuses as they may be employed with the photonic treatment table shown in FIG. 11.
Figure 12:
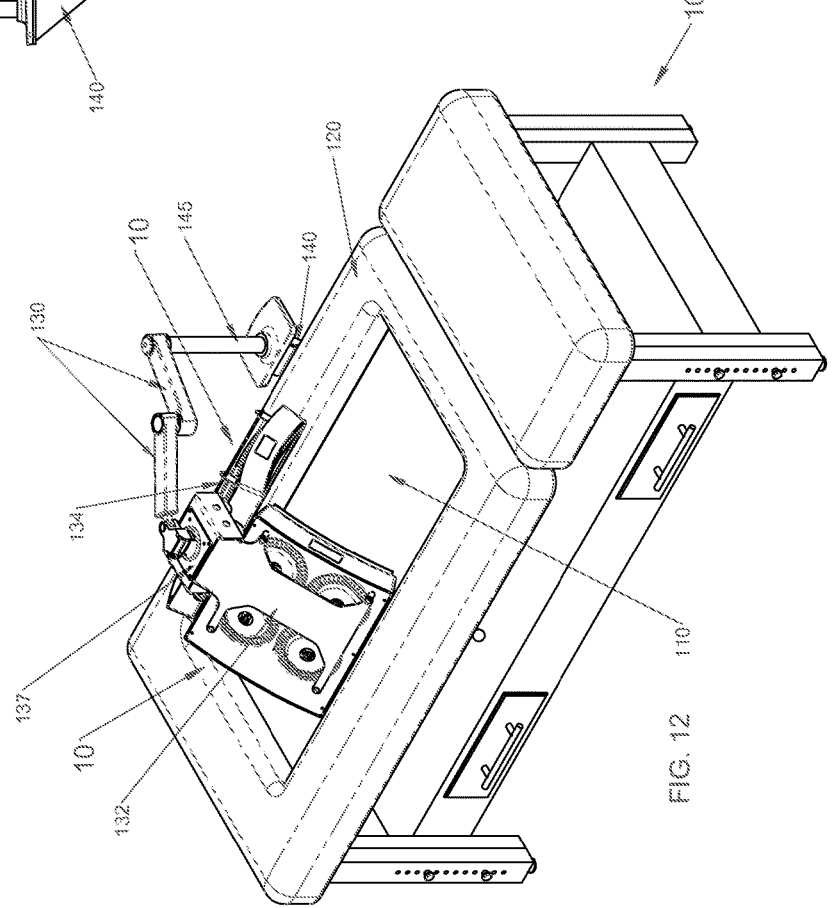
FIG. 12 is a perspective view of an embodiment of a series of two photonic treatment apparatuses as they may be employed with the photonic treatment table in accordance with the present invention.

FIG. 7 illustrates the bottom view of the photonic treatment apparatus 10, wherein photonic engines 54 may be positioned, each having a plurality of LEDs 55 that energize the film 70 (e.g., a specific phosphor plate for a desired treatment) to customize the output to a specific wavelength necessary for treatment of specific conditions. The LEDs 55 may be positioned through a light plate 56 secured by fasteners 57. In various embodiments, a user may include various LEDs 55 to generate higher or lower wavelengths of light to drive the conversion through the film 70. Further, a lower plate 52 may be configured to be connected to the lower casing 50 by fasteners 53.

The photonic engines 54 create photonic pressure behind the film 70, that energize the film 70 such that a desired wavelength may be achieved.

In one embodiment, the film 70 (e.g., a phosphor plate) receives wavelengths from the top surface of the LED 55 in order to wavelength convert the light emitted from the LED 55. The light emitted by the LED 55 is blue, for example, in a first wavelength range of 400 to 460 nm. The film 70 (e.g., white, red, green, etc.) energizes the first wavelength, transforming it into a second wavelength range of 600 to 700 mm.

The film 70 may be tested and then matched with LEDs 55 having a certain peak wavelength to achieve a target color. For example, the film 70, may comprise a layer of phosphor that can emit yellow light when illuminated by a blue or UV light, or a red emitting film 70 can be used for adding warmth to a resulting white light. In some embodiments the film 70 can emanate a controlled amount of blue light, which can combine with red and yellow light to achieve a desired white light.

FIGS. 2, 4-5, and 7-8 illustrate a photonic aperture 58 positioned in the lower casing 50 of the photonic treatment apparatus 10. Such a photonic aperture 58 may define the boundary through which the one or more photonic engines 54 may treat the patient. In addition, the film 70 may be positioned in the aperture 75 above the photonic aperture 58. Accordingly, the film 70 may preferably be shaped to be larger than the photonic aperture 58 and also smaller in width than the aperture 75 to allow for ease of insertion and removal of the film 70.

Notably, the photonic engines 54 create photonic pressure behind the film 70 that ultimately energizes the film 70 such that a desired wavelength may be achieved through the use of the film 70. Accordingly, a first zone of wavelengths originates from the photonic engines 54 from behind the film 70 from the treatment area that energizes a second zone of wavelengths emanating from the film 70 between the film 70 and the treatment area such that the photonic treatment apparatus 10 may provide desired treatments using the second zone of wavelengths as customized by the desired film 70.

FIGS. 10-15 illustrate one embodiment of the photonic treatment apparatus 10 of the present invention as it may be employed with a treatment table 100 for facilitating simplified treatments of a desired target area of a user. The treatment table 100 may further include one or more cushions 120 for supporting a user as well as a translucent member 110, both supported by the legs of the treatment table 100. The treatment table 100 may also provide attachment surfaces (not shown) for attaching one or more brackets 140.

Employing one or more brackets 140, the photonic treatment apparatus 10 may be positioned above the treatment table 100 and cushion 120 as described in greater detail below. Accordingly, the photonic treatment apparatus 10 may be repositionally secured, via a mounting bracket 135, to an articulating arm 130 that is rotatably mounted to a post 145 supported by the bracket 140. The mounting bracket 135 of the articulating arm 130 may be comprised of a rigid material that allows for a known uniform attachment to provide support to one or more treatment apparatuses 10. For example, as can be seen in FIGS. 10-11, the mounting bracket 135 may be connected to a first mounting plate 132, which is fastened to the photonic treatment apparatus 10 by one or more fasteners 137.

Accordingly, the articulating arm 130 may take a variety of forms for selectively positioning and orienting the photonic treatment apparatus 10 in a desired area of interest with respect to the patient via multiple joints, knuckles, arms, etc. The bracket 140 may also take a variety of forms for securing the articulating arm 130 as required for a given application with the photonic treatment apparatus 10.

In another preferred and non-limiting embodiment, and as shown in FIGS. 12-17, one or more photonic treatment apparatuses 10, 12, 14, 16 may be employed according to the present invention. In the illustrated embodiment, there may be provided one or more photonic treatment apparatuses 10, 12, 14 positioned above the treatment table 100, wherein the concave sides of the devices are directed downward, and another fourth photonic treatment apparatus 16 is positioned below the treatment table, having its concave side directed upward. Accordingly, a technician may be able to treat multiple treatment targets and/or larger areas of interest simultaneously while a user is on the treatment table 100.

More specifically, as illustrated in FIGS. 12-15, a second photonic treatment apparatus 12 may be supported next to the photonic treatment apparatus 10 on one side and a third photonic treatment apparatus 14 may be supported next to the photonic treatment apparatus 10 on the opposite side. Accordingly, and similar to the embodiment described above, the photonic treatment apparatus 10 may be fastened to the first mounting plate 132 via fasteners 137 such that the photonic treatment apparatus 10 is provided with support from the articulating arm 130 through the connection between the first mounting plate 132 and the mounting bracket 135. In addition, an adjustable hinge 138 may be pivotally connected between the first mounting plate 132 of the photonic treatment apparatus 10 and the second mounting plate 134 of the second treatment apparatus 12. Likewise, another hinge 138 may pivotally connect the first mounting plate 132 to a third mounting plate 136 opposite the second mounting plate 134. The third mounting plate 136 may thus be fastened to the third photonic treatment apparatus 14 via fasteners 137 for stabilizing and adjustably securing the third photonic treatment apparatus 14. In a similar fashion, the second mounting plate 134 may be fastened to the second photonic treatment apparatus 12 via fasteners 137.

Figure 17:
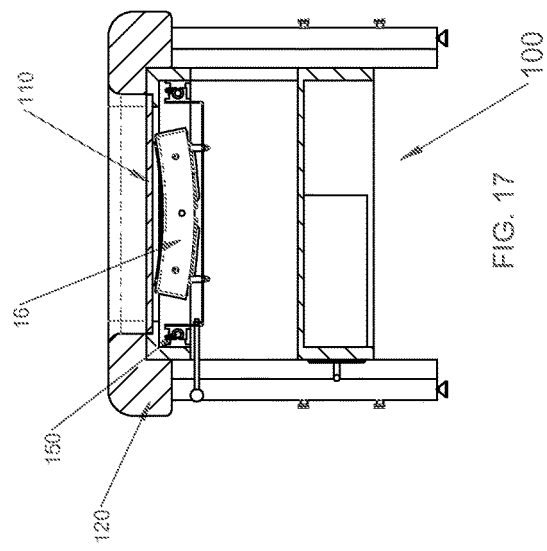
FIG. 17 is a front view of the photonic treatment apparatus as it may be employed with the photonic treatment table.
Figure 16:
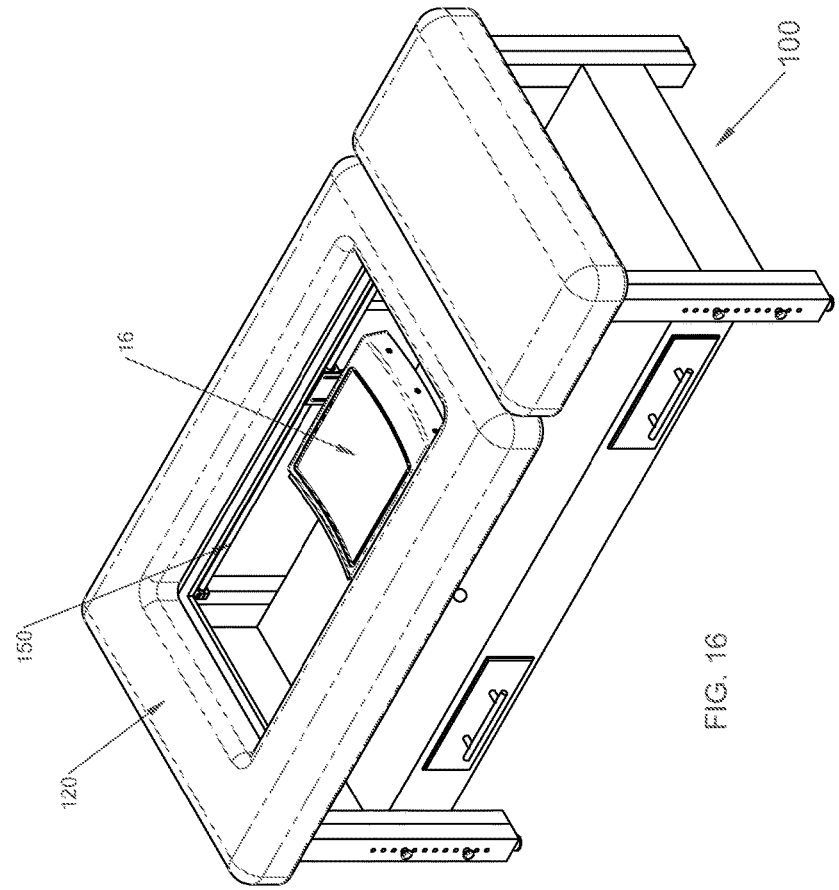
FIG. 16 is a partial cutaway rear view of the photonic treatment apparatus as it may be employed with the photonic treatment table.

As can also be seen in FIGS. 14-16, the fourth photonic treatment apparatus 16 may be positioned below the cushion 120 and translucent member 110. The fourth photonic treatment apparatus may also be mounted in close proximity to the translucent member 110 as shown in FIG. 17 for safe and sanitary close proximity treatments as preferred by the technician or based upon the needs of the patient user. Thus, rails 150 may be employed on the treatment table 100 so as to enable the fourth photonic treatment apparatus 16 under the cushions to travel nearly adjacent to the translucent member 110. Further, the fourth photonic treatment apparatus may be provided with a handle to assist in the translation of the fourth photonic treatment apparatus 16.

Accordingly, the present invention provides photonic treatment via one or more treatment apparatuses 10, 12, 14, 16 that allow for the selective positioning of photonic treatment of a user with respect to a treatment target and/or area of interest. Through the use of the novel integrated and adjustable hinges 138 as described herein, the photonic treatment apparatus 10 does not need to be brought to and from the patient for each and every treatment providing varying quality and reliability of desired treatments.

In a first step, after a patient is diagnosed with a treatable condition, the patient is positioned above a photonic treatment apparatus 16. Conditioned upon the location of the treatment area, the patient can be placed face up or face down. With reference to FIG. 14, when the patient is face up, the concave arrangement can focus light on an area comprising a majority of the body. For example, when abdominal treatment is required, the arrangement of photonic treatment apparatuses 10, 12, and 14 provide a substantially circular coverage.

In a second step, the film 70 is placed into the aperture 75 of the treatment apparatus 10. The type of film 70 is determined by diagnosis. Time of exposure also depends on the diagnosis. All apertures 75 of treatment apparatuses 10, 12, and 14 can have the same or different films 70.

Next, energy is created behind the film 70 that energizes a second zone of wavelengths emanating from the film 70. The wavelengths are focused on the treatment area. The treatment area may be small or large. The technician can use one or more photonic treatment apparatuses 10 simultaneously to treat the condition. The treatment apparatus 10 is selectively positioned with respect to the user. The adjustable hinges 138 in FIG. 14, or the rails 150 in FIG. 17 can be used to adjust the photonic treatment device.

In an optional step, in some embodiments, different combinations may be needed, either in simultaneous combination, or alternatively in sequence. Such combinations can be achieved by sliding the film 70 through the aperture 75. The various films 70 adjust the first wavelength energy, causing the second wavelength as it emits from the film 70. Optionally, various LEDs 55 can be used to cause higher or lower light wavelengths to be driven through the film 70, resulting in the ultimate combination suitable for the desired treatment and/or intensity.

Figure 18:
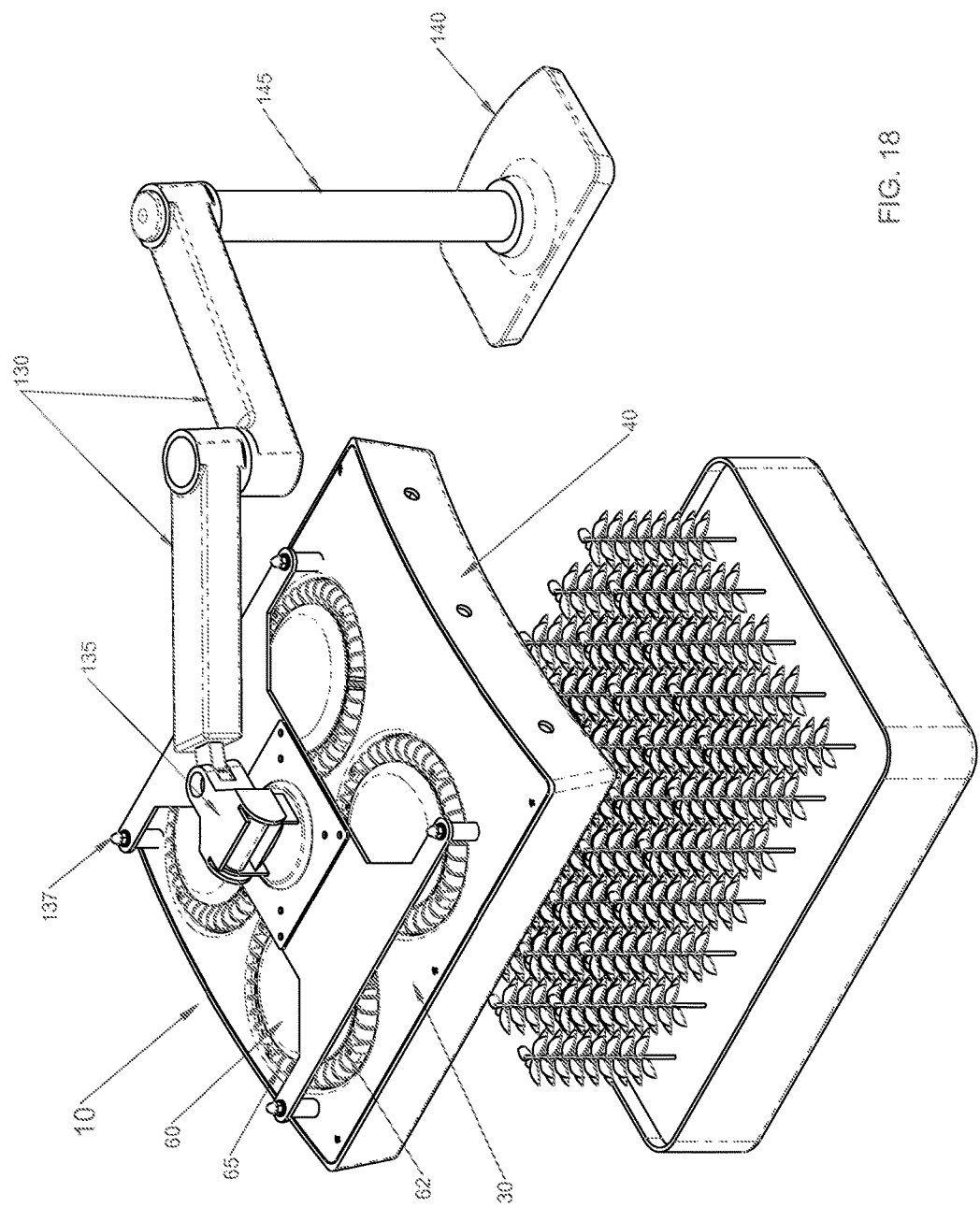
FIG. 18 is a perspective view of another embodiment of the photonic treatment apparatus as it may be used to grow plants.
Figure 19:
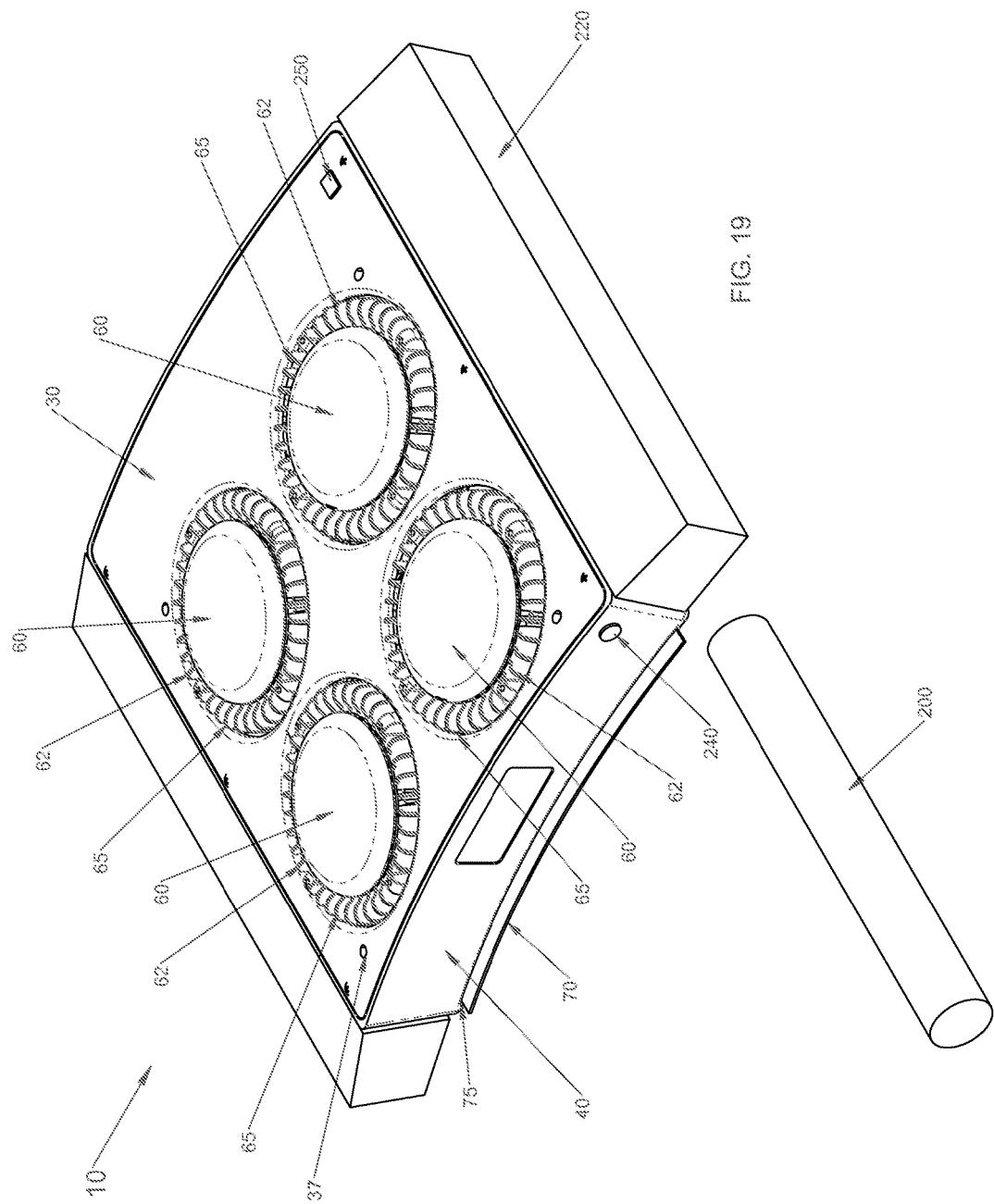
FIG. 19 is a perspective view of another embodiment of the present invention which illustrates how film can be automatically changed in the photonic treatment apparatus.

In another embodiment, as shown in FIG. 18, the photonic treatment apparatus 10 of the present invention may be used as a lighting source to grow plants. In such an embodiment, the film 70 can be replaced in the apparatus 10 to allow flexibility during the growing cycle. Without having to change the originating lighting source, the grower will have a choice of films 70 for adjusting the wavelengths to suit the needs of the sprouting, vegetative, and flowering stages along with the traditional lamps that indoor gardeners have depended on for years; the basic rules that should be followed to produce your desired yield.

Wavelengths of an approximately 350 to 550 (nm) spectrum provide a good start during the sprouting and vegetative stages. The specific strain of seed will determine if these cool spectrum lights are used for two to approximately eight weeks. The pre-flowering and flowering stages will be successfully induced with orange/red spectrum in the 540 to 700 nm range. The use of these hot spectrum lamps is combined with an increase of dark time of usually eight to twelve hours, with twelve hours being more typical.

In another embodiment, the film 70 can be automatically changed. Film boxes 220, 230 can be included on the photonic apparatus 10, which can contain a roll 200 of film, comprising multiple colors or formats of film 70 throughout the roll, which when energized exhibit different properties. The film is fed into the aperture 75 and an roller therein can be programmatically controlled by an onboard processor microcontroller 250 to wind or unwind according to needs, either manually or programmatically depending on the situation. The processor 250 can change the film 70 within the film roll 200 based on a predetermined time period, a countdown, or other indicia. For example, a program can include x amount of minutes on a first film 70 and y amount of minutes on a second film 70, where the x and y variables relate to the diagnosis of the patient, or the needs of the plants. The film 70 in the film roll 200 can also be changed manually by a manual advance button 240, located on the photonic apparatus 10.

Although the invention has been described in detail for the purpose of illustration based on what is currently considered to be the most practical and preferred embodiment (s), it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. Since other modifications and changes varied to fit particular operating requirements and environments will be apparent to those skilled in the art, the invention is not considered limited to the example chosen for purposes of disclosure, and covers all changes and modifications which do not constitute departures from the spirit and scope of this invention.

The invention claimed is:

1. A photonic treatment apparatus for patient care, comprising:
   one or more films;
   a casing comprising an aperture provided for the one or more films that are positioned within the apparatus to allow for selection of treatments of a user, wherein a film of the one or more films, when energized by a light, emits a wavelength;
   a photonic engine, positioned behind the film, to create photonic pressure, the photonic engine directed toward the film, wherein the photonic pressure comprises a first zone of wavelength emanations emitted from the photonic engine to energize the film to emit a second zone of wavelengths emanations from the film and the second zone of wavelength emanations directed toward a target area, wherein the second zone of wavelengths is different from and energized by the first zone of wavelength emanations, such that the photonic treatment apparatus provides treatment of the target area; and a processor embedded in the casing, the processor configured to receive situational indicia and control the film, wherein the one or more films are one or more phosphorous plate.

2. The photonic treatment apparatus of claim 1, wherein the one or more films comprise a first phosphorous film associated with a first treatment and a second phosphorus film associated with a second treatment.

3. The photonic treatment apparatus of claim 2, wherein a first modality of wavelength associated with the first phosphorous film is applied as treatment for a first variety of skin conditions.

4. The photonic treatment apparatus of claim 1, configured to treat a target area including a skin condition on a patient.

5. The photonic treatment apparatus of claim 4, configured to treat a skin condition including one or more of psoriasis, eczema, shingles, or acne.

6. The photonic treatment apparatus of claim 1, wherein the film provides multiple mode wavelengths to disassociate molecules for deeper penetration of light energy into the target area.

7. The photonic treatment apparatus of claim 1, wherein the photonic engine comprises a plurality of LEDs.

8. The photonic treatment apparatus of claim 7, wherein the plurality of LEDs includes a first LED capable of generating a first wavelength of light to drive a conversion through the film, a second LED capable of generating a lower wavelength of light than the first LED to drive a conversion through the film, a third LED capable of generating a wavelength of light higher than the first LED to drive a conversion through the film, or any combination thereof.

9. The photonic treatment apparatus of claim 1, wherein the second zone of wavelength emanations is in the 600-700 nanometer range.

10. The photonic treatment apparatus of claim 1, configured to irradiate the target area during a first period of time, at predetermined intervals.

11. The photonic treatment apparatus of claim 10, configured to treat the target area including one or more of psoriasis, eczema, shingles, or acne.

12. The photonic treatment apparatus of claim 1, wherein the processor is configured with a microcontroller to automatically control the movement of the one or more films through the casing.

13. A photonic apparatus, comprising:

a film roll and a casing comprising an aperture for one or more films, wherein the photonic apparatus includes the film roll therein for treatment, wherein the film roll includes a plurality of films that are positioned therein to allow for selection of treatments of a user, wherein a film of the plurality of films, when energized by a light, emit a wavelength;

a photonic engine, positioned behind the film of the plurality of films of the film roll, to create photonic pressure, the photonic engine directed toward the film to energize the film of the plurality of films to emit an associated wavelength emanation; and a processor comprising program instructions to receive situational indicia and control the movement of the film roll through the casing, wherein the film is energized to generate a zone of wavelength emanations emitted from the film directed toward a target area, wherein the processor is configured to receive the situational indicia and control the film roll based on the situational indicia to change the zone of wavelength emanations from a first wavelength associated with a first film of the plurality of films to a different wavelength associated with a different film of the plurality of films, wherein the plurality of films are a plurality of phosphorous plates.

* * * * *

UNITED STATES PATENT AND TRADEMARK OFFICE
CERTIFICATE OF CORRECTION

PATENT NO. : 10,342,991 B2
APPLICATION NO. : 14/882001
DATED : July 9, 2019
INVENTOR(S) : Anthony J. DiCesaro Page 1 of 1

It is certified that error appears in the above-identified patent and that said Letters Patent is hereby corrected as shown below:

In the Specification

Column 1, Line 7, Delete "61/062,522," and insert -- 62/062,522, --

Signed and Sealed this
Seventeenth Day of September, 2019

Andrei Iancu
*Director of the United States Patent and Trademark Office*